United States Patent
Xu et al.

(10) Patent No.: US 11,341,333 B2
(45) Date of Patent: May 24, 2022

(54) NATURAL LANGUAGE SENTENCE GENERATION FOR RADIOLOGY

(71) Applicant: Siemens Healthcare GmbH, Erlangen (DE)

(72) Inventors: Juan Xu, Beijing (CN); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 385 days.

(21) Appl. No.: 16/592,924

(22) Filed: Oct. 4, 2019

(65) Prior Publication Data

US 2020/0117712 A1    Apr. 16, 2020

(30) Foreign Application Priority Data

Oct. 12, 2018  (EP) ..................... 18200204

(51) Int. Cl.
*G06F 40/30*    (2020.01)
*G16H 15/00*   (2018.01)
*G06N 20/00*   (2019.01)

(52) U.S. Cl.
CPC ............ *G06F 40/30* (2020.01); *G06N 20/00* (2019.01); *G16H 15/00* (2018.01)

(58) Field of Classification Search
None
See application file for complete search history.

(56) References Cited

U.S. PATENT DOCUMENTS

| | | | |
|---|---|---|---|
| 9,767,557 B1* | 9/2017 | Gulsun | G06K 9/4628 |
| 2017/0293725 A1* | 10/2017 | Liu | G06F 16/24522 |
| 2017/0337329 A1* | 11/2017 | Liu | G16H 30/40 |
| 2019/0214118 A1* | 7/2019 | Reicher | G16H 30/20 |
| 2020/0043600 A1* | 2/2020 | Glottmann | G06N 3/0454 |
| 2020/0151871 A1* | 5/2020 | Putha | G06N 3/08 |

FOREIGN PATENT DOCUMENTS

EP    3229157 A1    10/2017

OTHER PUBLICATIONS

Faruqui, Manaal et al; "Retrofitting Word Vectors to Semantic Lexicons"; Jan. 1, 2015; Proceedings of the 2015 conference of the north american chapter of the association for computational linguistics: Human language technologies; pp. 1606-1615; Stroudsburg; PA; DOI: 10.3115/v1/N15-1184; pp. 1606, col. 1—p. 1613, col. 2.

(Continued)

*Primary Examiner* — Nafiz E Hoque (57) ABSTRACT

A natural language sentence is generated for a radiology report. One or more words are obtained where the one or more words were produced based on image processing of a radiology image. A computer implemented text analysis process is used to analyse the one or more words to generate a natural language sentence representing the radiology image. The natural language sentence is output. The computer implemented text analysis process includes: determining, for each of the one or more words, and using word modified embeddings, a vector representing the word; and determining, based on the determined one or more vectors, and using a text generator model, the natural language sentence.

15 Claims, 3 Drawing Sheets

(56) References Cited

OTHER PUBLICATIONS

Zhihui, Luo et al; "Corpus-based approach to creating a semantic lexicon for clinical research eligibility criteria from UMLS"; Mar. 1, 2010; Summit on translational bioinformatics; pp. 26-30; https://WWW.ncbi.nlm.nih.gov/pmc/articles/PMC3041551/pdf/amia-s2010_cri_026.pdf; pp. 26; col. 1—pp. 30 col. 1.
Mostafazadeh, et al.; "Generating natural questions about an image." arXiv preprint arXiv:1603.06059 (2016).
Xu, et al.; "Show, attend and tell: Neural image caption generation with visual attention." International conference on machine learning. 2015.
Siemens Healthcare GMBH: "Syngo Dynamics—Online Help—Portal Manual"; 2015; VA 20; pp. 1-146.
Kisilev, et al.; "Semantic Description of Medical Image Findings: Structured Learning Approach"; 2015; p. 171.1-171.11; DOI https://dx.doi.org/10.5244/C.
Extended European Search Report (EESR) dated Apr. 23, 2019 in corresponding European Application No. 18200204.8.

* cited by examiner

NATURAL LANGUAGE SENTENCE GENERATION FOR RADIOLOGY

RELATED CASE

This application claims the benefit of EP 18200204, filed on Oct. 12, 2018, which is hereby incorporated by reference in its entirety.

TECHNICAL FIELD

The present embodiments relate to sentence generation, and more particularly to sentence generation using computer implemented text analysis processes.

BACKGROUND

Medical text reports, for example radiology reports, are used in the medical field to communicate information between medical professionals. For example, a patient's physician may refer a patient for certain medical imaging, for example Computed Tomography Angiography (CTA). A radiographer then carries out the medical imaging of the patient, and a radiologist then reads or interprets the resulting image to produce a text-based radiology report of their findings, typically written using natural language sentences. The radiology report is then provided to the referring physician. The referring physician may then make a diagnosis of a condition of the patient based on the radiology report.

Known Artificial Intelligence (AI) based image analysis algorithms analyse medical images to detect anomalies, detect anatomical entities, segment and quantify organ sizes, or classify abnormalities into various types, and the like. Different AI algorithms are trained for different specific tasks. The output of a given AI algorithm generally includes a structured and quantitative table of findings including numerical or categorical variables.

U.S. Pat. No. 9,767,557B1 (Siemens Healthcare GmbH) discloses a Recurrent Neural Network (RNN) Long Short-Term Memory (LSTM) based plaque detection AI algorithm that may be applied to Coronary CT Angiography images to detect plaques, and output classification results relating to the image. The classification result may be a multi-class label. e.g., for plaque type classification (e.g., calcified, non-calcified, mixed), or a continuous value, e.g., for stenosis grading regression.

However, it may be difficult for the referring physician, or other consumers of the information, to interpret the output of the AI algorithm. Converting the AI image processing algorithm output to natural language sentences would alleviate this problem.

A known method of converting radiological findings to natural language sentences is for a radiologist to use pre-defined macros in a dictation system that automatically populates narrative text into a report based on keywords. These macros are hard-coded and individually defined, thereby requiring extensive manual effort to create. The macros are further not adaptable to situations that may be different from the intended rule at the time the macro was created and are not able to create narrative sentences when only partial information is provided to them.

It is therefore desirable to provide for an efficient, flexible and reliable method of generating natural language sentences from data obtained from radiological image analysis.

SUMMARY

According to a first aspect, there is provided a method of generating a natural language sentence for a radiology report, the method including: obtaining one or more words, the one or more words having been produced based on image processing of a radiology image; analysing, using a computer implemented text analysis process, the one or more words, to generate a natural language sentence representing the radiology image; and outputting the natural language sentence; wherein the computer implemented text analysis process includes: determining, for each of the one or more words, and using word embeddings, a vector representing the word; and determining, based on the determined one or more vectors, and using a text generator model, the natural language sentence; and wherein the word embeddings are word embeddings that have been generated by modifying first word embeddings based on first data, the first word embeddings having been generated based on one of a first corpus and a second corpus, the first data having been generated based on the other of the first corpus and the second corpus, the first corpus including text from one or more radiology reports, the second corpus being different to the first corpus and including plain language text.

Optionally, the first data includes second word embeddings, the second word embeddings having been generated based on the other of the first and second corpus, and the word embeddings are word embeddings that have been generated by modifying the first word embeddings based on the second word embeddings.

Optionally, the word embeddings are word embeddings that have been generated by, for a given word embedding for a given word, concatenating a vector of the first word embedding for the given word with a vector of the second word embedding for the given word to produce a modified vector for the given word.

Optionally, the first data includes a semantic lexicon, the semantic lexicon having been generated based on the other of the first and second corpus, and the word embeddings are word embeddings that have been generated by modifying the values of the vectors of the first word embeddings based on the semantic lexicon.

Optionally, the method includes: generating the first word embeddings and first data; and modifying, based on the first data, the first word embeddings, thereby to generate the word embeddings used for determining the vector representing each word.

Optionally, the method includes: training the text generator model based on a database of training data, the training data including groups of one or more words, each group being annotated with a ground-truth corresponding to a natural language sentence.

Optionally, the method includes: determining, using a first said text generator model, and based on the one or more obtained words, a first natural language sentence; and determining, using a second, different, said text generator model, and based on the one or more obtained words, a second natural language sentence.

Optionally, the second natural language sentence is in a different language to the first natural language sentence.

Optionally, the method includes: outputting the first natural language sentence in a first radiology report; and outputting the second natural language sentence in a second radiology report, different to the first radiology report.

Optionally, the method includes: training the first text generator model based on first training data; and training the second text generator model based on second training data different to the first training data.

Optionally, the method includes: analysing an output of a computer implemented image analysis process performed on a radiology image to determine the one or more words.

Optionally, the method includes: performing a computer implemented analysis process on the radiology image to provide the output of the image analysis process.

According to a second aspect, there is provided an apparatus including a processor and memory, the processor and the memory being arranged to perform method according to the first aspect.

Optionally, the apparatus is a medical imaging scanner.

According to a third aspect, there is provided a computer readable medium having instructions stored thereon which when executed by a computer cause the computer to perform the method according to any the first aspect.

Further features and advantages of the invention will become apparent from the following description of preferred embodiments of the invention, given by way of example only, which is made with reference to the accompanying drawings.

DETAILED DESCRIPTION

Figure 1:
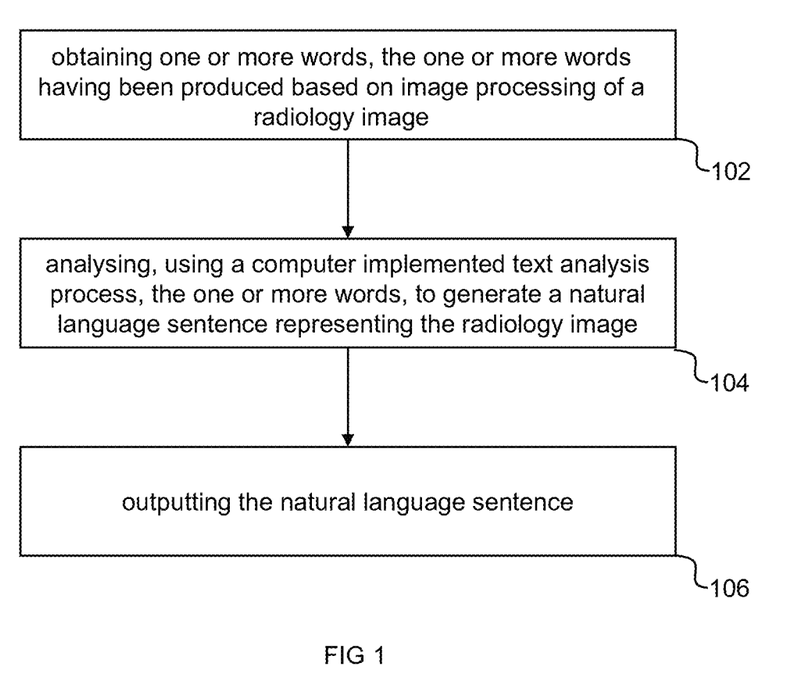
FIG. 1 is a flow diagram that illustrates schematically a method according to an example.

FIG. 1 illustrates schematically a flow diagram of acts of a method of generating a natural language sentence for a radiology report, according to an example.

Referring to FIG. 1, the method includes, in act 102, obtaining one or more words, the one or more words having been produced based on image processing of a radiology image.

For example, the radiology image may be an image obtained by performing medical imaging using a medical imaging scanner. For example, the medical imaging used to obtain the radiology image may include Computed Tomography (CT) scanning, for example Computed Tomography Angiography (CTA), or may include, for example, Magnetic Resonance Imaging (MRI), for example stress perfusion cardiac MRI, or the like.

In some examples, the image processing of the radiology image to produce the one or more words may include analysis by a human. For example, a radiologist may read or interpret the radiology image and provide one or more keywords representing the image or more or more medical findings thereof. For example, referring to FIG. 2, a first example method 208 of producing the one or more words may include a radiologist analysing 204 one or more radiology images 202 to provide a table of visual key words 206. In this example, the visual keywords representing the images 202 or relevant findings thereof are "moderate stenosis", "mid-portion" and "calcified atherosclerotic". In this example, the one or more words may be obtained by the radiologist entering the words into a computer using a keyboard, or by dictation using voice-to-text software, or by web-form for example including one or more drop down menus, or the like. The radiologist may therefore enter the findings of the analysis of the image as one or more key words, as opposed to natural language sentences. This may improve the efficiency of radiological image analysis.

In some examples, the image processing of the radiology image to produce the one or more words may include a computer implemented image analysis process. In some examples, the method may include performing the computer implemented analysis process on the radiology image to provide an output of the image analysis process.

In some examples, the computer implemented image processing may include Artificial Intelligence (AI)-based image processing. For example, the radiology image may be a Coronary CT Angiography. A Recurrent Neural Network (RNN) Long Short-Term Memory (LSTM) based plaque detection AI algorithm may be applied to Coronary CT Angiography images to detect plaques, for example as described in U.S. Pat. No. 9,767,557B1. The output of this algorithm may be a classification result, which may be a multi-class label e.g., for plaque type classification (e.g., calcified, non-calcified, mixed), and/or a continuous value, e.g., for stenosis grading regression.

Figure 2:
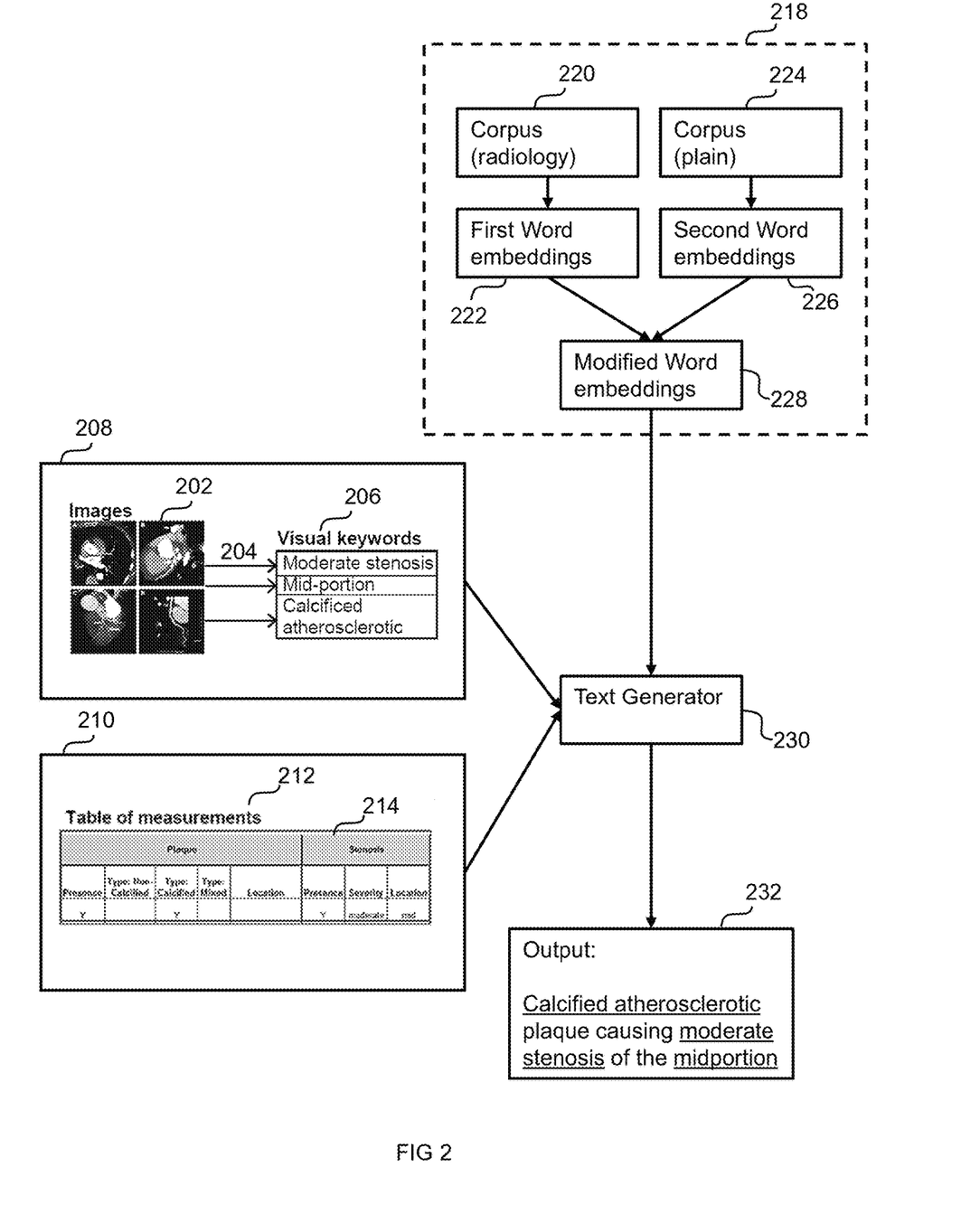
FIG. 2 is a diagram that illustrates schematically functional units according to an example.

For example, referring to FIG. 2, a second example method 210 of obtaining the one or more words includes obtaining a table of measurements 212 output from an AI based image processing algorithm. As with the first method, in this example, the image(s) (not shown) processed by the AI-based image processing algorithm to produce the table of measurements 212 are Coronary CT Angiography images. In the example of FIG. 2, the table of measurements 212 includes multiclass labels 214, in this example: plaque presence; plaque type classification (calcified, non-calcified, mixed); plaque location; and stenosis presence, severity and location. In the example of FIG. 2, the table of measurements 212 indicates that a plaque is present (there is a "Y" in the plaque presence field), that it is a calcified plaque (there is a "Y" in the "Type: Calcified" field), that there is a stenosis (there is a "Y" in the stenosis presence field), that the stenosis is moderate (there is the word "moderate" in the "severity" field) and that the location is in the mid-portion (there is the word "mid" in the "location" field).

In some examples, the method may include analysing an output of the computer image analysis process performed on a radiology image to determine the one or more words. For example, the one or more obtained words may be determined based on the table of measurements 212 (or data represented thereby). For example, based on the presence of the "Y" in the "Plaque//type: calcified" field, the presence of "moderate" in the "Stenosis//Severity" field, and the presence of "mid" in the "Stenosis//Location" field, the one or more words may be determined to be "calcified plaque", "moderate stenosis", and "mid-portion". These determined words may be the one or more words obtained in act 102 of the method of FIG. 1.

It will be appreciated that in some examples, the one or more words may be obtained based on any suitable computer implemented image analysis processes. For example, the one or more obtained words may be produced by other AI image processing algorithms applied to other forms of radiology images. For example, the radiology image may be a Chest CT scan, and the image processing algorithm may be a Convolutional Neural Network (CNN) based lung nodule detection. As another example, the radiology image may be a Multi-parametric Prostate MRI, and the image processing algorithm may be an Adversarial Image-2-Image Deep Learning for segmentation and lesion detection algorithm, for example.

In any case, one or more words, having been produced based on image processing of a radiology image, are obtained.

Referring again to FIG. 1, the method includes, in act 104, analysing, using a computer implemented text analysis process, the one or more words, to generate a natural language sentence representing the radiology image.

The computer implemented text analysis process of act 104 includes determining, for each of the one or more words, and using word embeddings, a vector representing the word; and determining, based on the determined one or more vectors and using a text generator model, the natural language sentence.

Word embeddings may be mappings of individual words or phrases of a vocabulary onto real-valued vectors representative thereof in a vector space. Each vector may be a dense distributed representation of the word in the vector space. Word-embeddings may be learned/generated to provide that words or phrases that have a similar meaning have a similar representation in vector space.

Word embeddings may be learned using machine learning techniques. Word embeddings may be learned/generated for words of a vocabulary of a corpus of text. Word embeddings may be learned/generated using a training process applied on the corpus of text. The training process may be implemented by a deep learning network, for example based on a neural network. For example, the training may be implemented using a Recurrent Neural Network (RNN) architecture, in which an internal memory may be used to process arbitrary sequences of inputs. For example, the training may be implemented using a Long Short-Term Memory (LSTM) based Recurrent Neural Network (RNN) architecture, for example including one or more LSTM cells for remembering values over arbitrary time intervals, and/or for example including gated recurrent units (GRU). The training may be implemented using a convolutional neural network (CNN). Other suitable neural networks may be used.

Various models may be employed for the training process for learning/generating word embeddings. For example, word embeddings may be learned using a skip-gram model implemented on a neural network. The skip-gram model may learn word embeddings for words given the local usage context of the words, where the context is defined by a window of neighbouring words. This window is a configurable parameter of the model. The skip-gram model may learn the word embeddings by predicting words that surround a given word. For example, all words of a corpus of text may be used to build a vocabulary. The word embeddings may initially map each word onto a vector of a given dimensionality that is populated with randomly generated numbers. The skip-gram model may take a word of the vocabulary and using the word embedding associated with that word attempt to predict words that surround that word in a given window. The skip-gram model may then compare the predictions with words that actually surround that word in the corpus of text and adjust word embeddings accordingly on the basis thereof. This process may be recursively applied until accurate word embeddings are generated. Other suitable models for learning word embeddings may be applied. The vector mapped by the word embeddings may be dense, i.e. of relatively low dimension, for example as compared to sparse word representations, allowing for efficient implementation.

The word embeddings used to determine the vectors in the computer implemented text analysis process of act 104 of FIG. 1, are modified word embeddings. That is, the word embeddings are word embeddings that have been generated by modifying, based on first data, first word embeddings. The first word embeddings was generated based on one of a first corpus and a second corpus. The first data was generated based on the other of the first corpus and the second corpus. The first corpus includes text from one or more radiology reports, and the second corpus is different to the first corpus and includes plain language text.

In one example, the first data may include second word embeddings. The second word embeddings may be generated based on the other of the first and second corpus than the one of the first corpus and a second corpus on the basis of which the first word embeddings are generated. The modified word embeddings may be word embeddings that have been generated by modifying the first word embeddings based on the second word embeddings.

For example, and as illustrated in FIG. 2, first word embeddings 222 may be generated by applying a training process, for example as described above, on the first corpus 220 including text from one or more radiology reports. For example, a plurality, for example hundreds, or thousands, of radiology reports may be extracted from a database, and the word-embeddings training process applied to (for example exclusively to) the text of the radiology reports produce the first word embeddings. In some examples, the first word embeddings used may be pre-trained word embeddings and be extracted from a database. The vectors of the first word embeddings may capture or represent in vector space the meaning or context of words of the lexicon of radiology, and as used in radiology reports.

The second word embeddings 226 may be generated by applying a training process, for example as described above, on the second corpus 224 including plain language text. For example, the second corpus may include text that is not extracted from radiology reports. For example, a plurality, for example hundreds, or thousands, of web articles, or other machine-readable plain text documents may be extracted from a database, and the word-embeddings training process applied to (for example exclusively to) the text of those documents produces the second word embeddings. In some examples, the second word embeddings used may be pre-trained word embeddings and extracted from a database. The vectors of the second word embeddings may capture or represent in vector space the meaning or context of words of the lexicon of plain language, and as used in natural language sentences.

As mentioned, the vectors of the first word embeddings may capture or represent in vector space the meaning or context of words of the lexicon of radiology, and as used in radiology reports. However, the language of radiology reports may be terse and matter-of-fact. The first word embeddings alone may therefore not accurately capture nuances of plain language, for example in relation to accurate sentence generation. On the other hand, the vectors of the second word embeddings may capture or represent in vector space the meaning or context of words of the lexicon of plain language, and as used in natural language sentences. However, the second word embeddings alone may not accurately capture the lexicon and proper context and meaning of words as used in radiology reports. The word embeddings used in act 104 of the method of FIG. 1 being modified word embeddings 228 that have been generated by modifying one of first 222 and second 226 word embeddings based on the other of the first 222 and second word 226 embeddings allows for the sentences generated based thereon to accurately represent the meaning or context of words used in radiology reports, but with the nuances of plain language.

In some examples, the modified word embeddings 228 may be word embeddings that have been generated by, for a given word embedding for a given word, concatenating a vector of the first word embedding 222 for the given word with a vector of the second word embedding 226 for the given word to produce a modified vector for the given word. For example, the first word embeddings 222 may include, for each word of a first vocabulary, a 300-dimensional vector representing the word in vector space. Similarly, the second word embeddings 226 may include, for each word of a second vocabulary, a 300-dimensional vector representing the word in vector space. A modified word embedding 228 for a given word may be generated by concatenating (i.e. chaining) the vector for that word from the first word embeddings with the vector for that word from the second word embeddings (or vice versa), thereby to generate a 600-dimensional vector for that word, for example. The modified word embedding 228 therefore captures, in vector space, the meaning and usage of that word simultaneously in both radiological and plan language contexts. If a word is present in one, but not the other, of the vocabulary of the first and second word embeddings, then the vector for the word embedding in which the word is not in the vocabulary may be assigned zero values, in this example 300 zeros. For example, this may result in a 600-dimensional modified word embedding vector that concatenates the 300-dimensional vector of the first (or second) word embedding for that word with 300 zero values. This may occur, for example, if a word is only used in the radiology language corpus, for example a word specific to the radiological lexicon that does not find usage in the plain language corpus. This may allow specific words to still be accounted for in the modified word embeddings. Generating the modified word embeddings 228 by concatenation may be computationally inexpensive and hence an efficient method of generating modified word embeddings to be used the sentence generation.

In other examples (not illustrated), the first data may include a semantic lexicon. The semantic lexicon may have been generated based on the other of the first and second corpus than the one of the first corpus and a second corpus on the basis of which the first word embeddings have been generated. The word embeddings may be word embeddings that have been generated by modifying the values of the vectors of the first word embeddings based on the semantic lexicon.

A semantic lexicon may be a dictionary of words labelled with semantic classes. The semantic lexicon may be generated based on the corpus of radiology reports, or the plain language corpus. In some examples, the semantic lexicon may be generated based on supervised or unsupervised machine learning based on the corpus. In some examples, the technique as described in "Luo et al; Corpus-based Approach to Creating a Semantic Lexicon for Clinical Research Eligibility Criteria from UMLS; Summit on Translat Bioinforma. 2010; 2010: 26-30" may be used to process the corpus to identify semantic units, or lexemes (e.g. words), retrieving a concept unique identifier for the identified units from a database, and then tagging or labelling the identified units with an appropriate semantic class, thereby to generate the semantic lexicon. In some examples, the semantic lexicon, generated based on radiology reports or plain language, may be obtained from a database. For example, the semantic lexicon may be pre-generated and retrieved from a database for use in generating the modified word embeddings. In some examples, generating the modified word embeddings may include retrofitting or refining the first or second word embeddings based on the semantic lexicon. For example, using the technique as described in "Faruqui et al; Retrofitting Word Vectors to Semantic Lexicons; https://arxiv.org/pdf/1411.4166.pdf" a semantic lexicon may be represented as a knowledge graph including one vertex for each word and edges indicating a semantic relationship between the words. The word embeddings associated with each word in the knowledge graph may be modified iteratively based on the word embeddings of its neighbours, to reduce the distance therebetween. Word embeddings for words of the knowledge graph (i.e. words of the semantic lexicon) that do not have a word embedding may be determined during this process by initially assigning the vectors with zero values and allowing the vector values to develop during the iterative modification of the existing word embeddings.

Modified word embeddings may thereby be generated which better capture and reflect the semantic relationships as defined by the semantic lexicon, and/or which include additional word embeddings for words from the semantic lexicon. For example, the first word embeddings may be generated based on plain language text, and the semantic lexicon may be generated based on radiology reports. In this case, the word embeddings derived from the plain language text will be modified to account for semantic relationships as used in a radiology-specific context and/or words specific to radiology. As another example, the first word embeddings may be generated based on radiology reports, and the semantic lexicon may be generated based on plain language text. In this case, the word embeddings derived from the radiological text will be modified to account for semantic relationships as used in a plain language context.

Generating the modified word embeddings based on modifying word embeddings based on using a semantic lexicon, for example as described above, may allow for modified word embeddings that capture both radiology specific contexts and the nuances of plain language, but without increasing the number of dimensions of the vectors of the word embeddings. For example, the first word embeddings may have 300-dimensional vectors, and the modified word embeddings may still have 300-dimensional vectors. This may allow for efficient generation of sentences based on the modified word embeddings.

In some examples, the method may include, for example as part of a training phase, generating or otherwise obtaining the first word embeddings and first data (for example as described above), and modifying, based on the first data, the first word embeddings (for example as described above), thereby to generate the word embeddings used for determining the vector representing each word.

As mentioned, the computer implemented text analysis process of act 104 includes determining, for each of the one or more words, and using word embeddings (i.e. the modified word embeddings as described above), a vector representing the word. The computer implemented text analysis process of act 104 also includes determining, based on the determined one or more vectors, and using a text generator model, the natural language sentence. For example, as illustrated in FIG. 2, the text generator model 230 has, as inputs, the one or more words 206 obtained from image processing of the radiology image 202, and the modified word embeddings 228, and may output a natural language sentence 232 representing the image 202.

The text generator model 230 may be a model for determining a natural language sentence for the obtained one or more words based on the vector representations of the one or more words. The text generator model 230 may apply a function to the vectors from modified word-embeddings of the obtained one or more words, and determine based on an output of that function a natural language sentence representing the image based on which the one or more words were obtained. For example, the function may map the vectors from word-embeddings for the obtained one or more words onto a natural language statement. For example, the text generator model 230 may encode the vectors of each of the obtained one or more words into a vector representing the one or more words, for example using a neural network, and the text generator model may map the vector representing the one or more words onto a natural language sentence. The text generator model 230 may be based on or implemented using a deep learning network, for example a neural network, for example a Recurrent Neural Network (RNN) architecture, in which an internal memory may be used to process arbitrary sequences of inputs, for example a Long Short-Term Memory (LSTM) based Recurrent Neural Network architecture, for example including one or more LSTM cells for remembering values over arbitrary time intervals, and/or for example including gated recurrent units (GRU). The text generator model 230 may be implemented using a convolutional neural network (CNN). The neural network may include an attention model, which may allow for the text generator model 230 to attend to different parts (e.g. different words) of the input one or more words differently. Other suitable neural networks may be used.

The text generator model 230 may be trained using a training process to determine appropriate natural language sentences for given input one or more words. For example, the function may be trained to map the vectors from the word-embeddings for the one or more words onto an appropriate sentence.

The training process may be implemented using a deep learning network, for example based on a neural network, for example any one or more of the example neural networks described above.

The text generator model training process may include machine learning techniques.

In some examples, the training process may include supervised learning. The supervised learning may include inferring the function from annotated training data including training examples. For example, the method may include training the text generator model based on a database of training data, the training data including groups or sets of one or more words, each group or set being annotated with a ground-truth corresponding to a natural language sentence. That is, the training may be based on a database of sets of one or more words, each set being annotated with a ground-truth corresponding to a sentence (i.e. sentence to be given by the text analysis process). For example, the supervised learning may be based on a database of sets of one or more words of a corpus of radiology reports, each set being annotated (for example by a radiologist or other physician) with a ground-truth corresponding to a natural language sentence accurately representing the set of words. The sets of words and/or sentences may be from a plurality of radiology reports pre-collected as a training data set and corpus for the training process. Each set of one or more words of the training data may represent an input object, and the corresponding ground-truth sentence a supervisory signal, for the training process. The training process may analyse the training data to produce an inferred function, which may then be used for determining a natural language sentence for a given input set of one or more words.

Referring to FIG. 1, the method includes, in act 106, outputting the natural language sentence. For example, as illustrated in FIG. 2, the text generator model 230 outputs the natural language sentence 232. In this example, based on the obtained one or more words 206 being "moderate stenosis", "mid portion", and "calcified atherosclerotic", the text generator model 230 outputs the natural language sentence "Calcified atherosclerotic plaque causing moderate stenosis of the midportion". The output may be stored in a storage device (memory), or may for example be transmitted to a device (not shown) which may itself store or further process the natural language sentence. For example, the natural language sentence may be output into a radiology report document. The radiology report document may be, for example, transmitted to a terminal of the referring physician, or other consumer, so that the natural language sentences of the radiology report can be read and appreciated. For example, the referring physician may make a diagnosis based on the natural language sentences. This may be more reliable and efficient than the referring physician or other consumer making judgements or otherwise using the information contained in the radiology report, as compared to interpreting the keywords or table of measurements output from the image analysis.

The text generator model 230 may produce a natural language sentence, based on the words 206 obtained from the image processing of the radiology images, which sentence both represent the image by containing key information therefrom and captures the nuance of natural language. Reliable and accurate natural language sentence production may therefore be provided. An appropriate natural language sentence may be produced by the text generator model under a variety of conditions, for example which may not depend on the number or type of words input, and therefore may provide a flexible method of providing natural language sentences, for example as compared to hard coding macros for sentence generation.

In some examples, the method may include determining multiple sentences using respective multiple text generator models (not shown). For example, the method may include determining, using a first said text generator model, and based on the one or more obtained words, a first natural language sentence; and determining, using a second, different, said text generator model, and based on the one or more obtained words, a second natural language sentence.

For example, the first text generator model may be trained differently to the second text generator model. For example, the method may include: training the first text generator model based on first training data; and training the second text generator model based on second training data different to the first training data. For example, the first text generator model may be trained based on training data that has, for given sets of one or more words, first ground truth sentences, and the second text generator model may be trained based on training data that has, for the given sets of one or more words, second ground truth sentences.

In some examples, the ground truth sentences used for training a particular one of the text generator models may be selected according to a given audience or recipient of the natural language sentences (and in turn the radiology report). For example, a first audience may be a referring physician and a second audience may be a patient. It may be that the patient requires a different level of detail in the radiology report as compared to the referring physician. The first ground truth sentences may therefore include more radiological detail, whereas the second ground truth sentences may be more based on plain language. Therefore, for the same set of obtained input words (from analysis of the radiology image), the first text generator may output radiologically detailed sentences for a radiology report for the referring physician, and the second text generator may output less radiologically detailed sentences for a radiology report for the patient.

In some examples, the second natural language sentence may be in a different language to the first natural language sentence. For example, this may allow for radiology reports to be produced that accommodate for different languages.

For example, the first text generator model may be trained based on training data that has, for given sets of one or more words, first ground truth sentences in a first language, and the second text generator model may be trained based on training data that has, for the given sets of one or more words, second ground truth sentences in a second language. It will be appreciated that sentences in different languages could be obtained by translating the sentence output by the text generator model into different languages. However, this may not accurately capture the context and meaning of the original sentence. On the other hand, vectors representing the words in word embeddings are language independent, and capture the context and meaning of words as used in the language on which they were trained. Therefore, the one or more input words may be in a first language, but the meaning and context of the words, as conveyed through the word embeddings used in a text generator model that has been trained based on ground truth sentences in a second language, will be present in the output of the text generator model in the second language. This enables accurate radiology reports to be produced in multiple languages based on input one or more words in a single language. This may provide flexibility.

In some examples, the method may include outputting the first natural language sentence in a first radiology report; and outputting the second natural language sentence in a second radiology report, different to the first radiology report. For example, the first radiology report may be stored separately or transmitted to different recipients as the second radiology report. That may be useful, as described above, for providing radiology reports including sentences with different levels of detail, or in different languages, to different recipients as appropriate, as described above.

Figure 3:
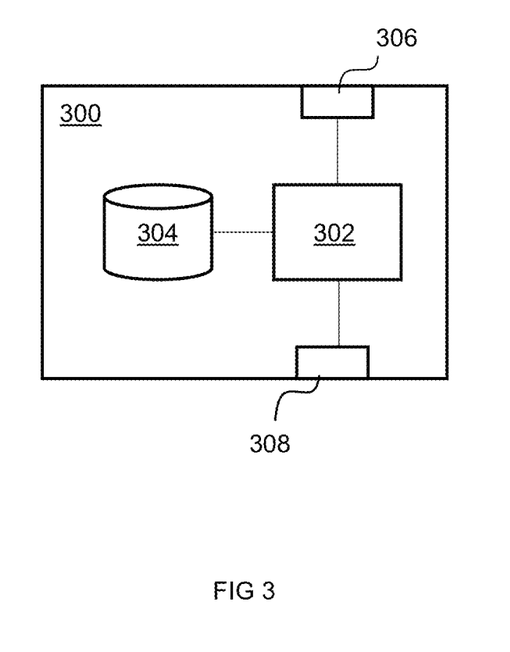
FIG. 3 is a diagram that illustrates schematically an apparatus according to an example.

FIG. 3 illustrates schematically an example apparatus 500, by which the method described above with reference to FIG. 1 or 2 may be performed or implemented. The apparatus 300 includes a processor 302 and a memory 304. The memory 304 may store instructions which when executed by the processor 302 cause the apparatus 300 to perform the method according to any one or combination of the examples described above with reference to FIG. 1 or 2. For example, the apparatus 300 may be arranged to implement the narrative text generator model 230, or the modification of word embeddings 218 of FIG. 2. The apparatus includes an input 306 and an output 308. For example, the input 206 may be arranged to receive a radiology image, one or more words obtained from image processing of a radiology image, one or more word embeddings, modified word embeddings, semantic lexicons, radiology reports or text thereof, and/or plain language text, as described above, for example from a storage unit (not shown) or transmitted from one or more other devices (not shown). The output 308 may output one or more natural language sentences, and/or one or more radiology reports, as described above, for example to a storage means (memory) (not shown) or for transmission to one or more further devices (not shown).

In some examples, the apparatus may be a medical imaging scanner (not shown). For example, the apparatus may include an imaging unit (not shown) for capturing radiology images, which may be provided to the processor 302. The processor 302 may then apply image analysis to the radiology images, for example as described above, to provide one or more key words representing the image, and the processor 302 may then apply the method as described with reference to FIG. 1 to provide the natural language sentences or radiology reports therefrom as appropriate. The apparatus 300 being or being part of a medical imaging scanner may allow that radiology reports, including accurate and reliable natural language sentences, are produced directly at the point of medial imaging. This may reduce the time required to produce radiology reports, and may improve workflows.

The above examples are to be understood as illustrative examples of the invention. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. A method of generating a natural language sentence for a radiology report, the method comprising:
 obtaining one or more words, the one or more words having been produced based on image processing of a radiology image;
 generating, using a computer implemented text analysis process of the one or more words, a natural language sentence representing the radiology image; and
 outputting the natural language sentence;
 wherein the computer implemented text analysis process comprises:
  determining, for each of the one or more words, and using modified word embeddings, a vector representing the word; and
  determining, based on the determined one or more vectors, and using a text generator model, the natural language sentence; and
 wherein the modified word embeddings are word embeddings that have been generated by modifying first word embeddings based on first data, the first word embeddings having been generated based on one of a first corpus and a second corpus, the first data having been generated based on the other of the first corpus and the second corpus, the first corpus comprising text from one or more radiology reports, the second corpus being different to the first corpus and comprising plain language text.

2. The method according to claim 1, wherein the first data comprises second word embeddings, the second word embeddings having been generated based on the other of the first and second corpus than the one of the first corpus and the second corpus on the basis of which the first word embeddings have been generated, and wherein the modified word embeddings are word embeddings that have been generated by modifying the first word embeddings based on the second word embeddings.

3. The method according to claim 2, wherein the modified word embeddings are word embeddings that have been generated by, for a given word embedding for a given word, concatenating a vector of the first word embedding for the given word with a vector of the second word embedding for the given word to produce a modified vector for the given word.

4. The method according to claim 1, wherein the first data comprises a semantic lexicon, the semantic lexicon having been generated based on the other of the first and second corpus than the one of the first corpus and the second corpus on the basis of which the first word embeddings have been generated, and wherein the modified word embeddings are word embeddings that have been generated by modifying the values of the vectors of the first word embeddings based on the semantic lexicon.

5. The method according to claim 1, further comprising:
generating the first word embeddings and the first data; and modifying, based on the first data, the first word embeddings, thereby to generate the modified word embeddings.

6. The method according to claim 1, further comprising:
training the text generator model based on a database of training data, the training data comprising groups of one or more words, each group being annotated with a ground-truth natural language sentence.

7. The method according to claim 1, wherein determining the natural language sentence comprises:
determining, using a first said text generator model, and based on the one or more obtained words, a first natural language sentence; and determining, using a second, different, said text generator model, and based on the one or more obtained words, a second natural language sentence.

8. The method according to claim 7, wherein the second natural language sentence is in a different language to the first natural language sentence.

9. The method according to claim 7, wherein outputting comprises:
outputting the first natural language sentence in a first radiology report; and outputting the second natural language sentence in a second radiology report, different to the first radiology report.

10. The method according to claim 7, further comprising:
training the first text generator model based on first training data; and training the second text generator model based on second training data different to the first training data.

11. The method according to claim 1, wherein obtaining the one or more words comprises:
analysing an output of a computer implemented image analysis process performed on a radiology image to determine the one or more words.

12. The method according to claim 11, wherein analysing the output comprises:
performing a computer implemented analysis process on the radiology image to provide the output of the image analysis process.

13. An apparatus comprising:
a processor and memory, the memory storing instructions, which when executed by the processor:
obtain one or more words, the one or more words having been produced based on image processing of a radiology image;

generate, using a computer implemented text analysis of the one or more words, a natural language sentence representing the radiology image; and output the natural language sentence;

wherein the computer implemented text analysis comprises:
determination, for each of the one or more words, and using modified word embeddings, a vector representing the word; and determination, based on the determined one or more vectors, and using a text generator model, the natural language sentence; and wherein the modified word embeddings are word embeddings that have been generated by modifying first word embeddings based on first data, the first word embeddings having been generated based on one of a first corpus and a second corpus, the first data having been generated based on the other of the first corpus and the second corpus, the first corpus comprising text from one or more radiology reports, the second corpus being different to the first corpus and comprising plain language text.

14. The apparatus according to claim 13, wherein apparatus is a medical imaging scanner.

15. A non-transitory computer readable medium having instructions stored thereon which when executed by a computer cause the computer to:
obtain one or more words, the one or more words having been produced based on image processing of a radiology image;

generate, using a computer implemented text analysis of the one or more words, a natural language sentence representing the radiology image; and output the natural language sentence;

wherein the computer implemented text analysis comprises:
determination, for each of the one or more words, and using modified word embeddings, a vector representing the word; and determination, based on the determined one or more vectors, and using a text generator model, the natural language sentence; and wherein the modified word embeddings are word embeddings that have been generated by modifying first word embeddings based on first data, the first word embeddings having been generated based on one of a first corpus and a second corpus, the first data having been generated based on the other of the first corpus and the second corpus, the first corpus comprising text from one or more radiology reports, the second corpus being different to the first corpus and comprising plain language text.

* * * * *